(12) United States Patent
Main et al.

(10) Patent No.: US 9,320,665 B2
(45) Date of Patent: Apr. 26, 2016

(54) RISK MODELING FOR PRESSURE ULCER FORMATION

(75) Inventors: Ian Main, Calgary (CA); Robert Miller, Calgary (CA); Terry Russell, Calgary (CA); Mitch Ousdahl, Calgary (CA)

(73) Assignee: XSENSOR Technology Corporation, Calgary (CA)

( * ) Notice: Subject to any disclaimer, the term of this patent is extended or adjusted under 35 U.S.C. 154(b) by 0 days.

(21) Appl. No.: 13/575,094

(22) PCT Filed: Jan. 27, 2011

(86) PCT No.: PCT/CA2011/000098
§ 371 (c)(1),
(2), (4) Date: Sep. 13, 2012

(87) PCT Pub. No.: WO2011/091517
PCT Pub. Date: Aug. 4, 2011

(65) Prior Publication Data
US 2013/0006151 A1    Jan. 3, 2013

Related U.S. Application Data

(60) Provisional application No. 61/298,716, filed on Jan. 27, 2010, provisional application No. 61/410,161, filed on Nov. 4, 2010.

(51) Int. Cl.
*A61B 5/103* (2006.01)
*A61G 7/057* (2006.01)
*A61B 5/00* (2006.01)

(52) U.S. Cl.
CPC ............... *A61G 7/057* (2013.01); *A61B 5/103* (2013.01); *A61B 5/447* (2013.01); *A61B 5/6891* (2013.01); *A61B 2562/0247* (2013.01);
(Continued)

(58) Field of Classification Search
CPC ........ A61B 5/4528; A61B 5/103; A61B 5/0053
USPC .................................................. 600/587, 595
See application file for complete search history.

(56) References Cited

U.S. PATENT DOCUMENTS 4,554,930 A * 11/1985 Kress .............................. 600/587
7,107,642 B2    9/2006 Wong et al.
(Continued)

FOREIGN PATENT DOCUMENTS

CN    101803983 A    8/2010
EP    2182339    5/2010
(Continued)

OTHER PUBLICATIONS

Office Action for Chinese Patent Application No. CN 201180007313.4, Dec. 31, 2013, 17 Pages.
(Continued)

*Primary Examiner* — Sean Dougherty
*Assistant Examiner* — Daniel Cerioni
(74) *Attorney, Agent, or Firm* — Fenwick & West LLP

(57) ABSTRACT

A method for modelling pressure exposure and/or the risk of pressure ulcer formation includes steps of using pressure sensors to derive pressure exposure or risk values and displaying the pressure exposure or risk values in a graphical manner to a user. Computer-implemented systems includes a pressure-sensing interface mat and components for implementing the steps of the methods.

26 Claims, 12 Drawing Sheets

(52) U.S. Cl.
CPC ...... *A61B 2562/046* (2013.01); *A61G 2203/34* (2013.01); *A61G 2203/46* (2013.01)

(56) References Cited

U.S. PATENT DOCUMENTS

| | | | |
|---|---|---|---|
| 7,378,975 B1* | 5/2008 | Smith et al. | 340/573.1 |
| 8,011,041 B2* | 9/2011 | Hann | 5/652.1 |
| 8,463,006 B2* | 6/2013 | Prokoski | 382/128 |
| 2005/0165284 A1* | 7/2005 | Gefen | 600/300 |
| 2005/0241409 A1 | 11/2005 | Taylor | |
| 2008/0275349 A1* | 11/2008 | Halperin et al. | 600/484 |
| 2009/0062693 A1* | 3/2009 | Woolfson et al. | 600/587 |
| 2009/0070939 A1* | 3/2009 | Hann | 5/652.1 |
| 2009/0209830 A1* | 8/2009 | Nagle et al. | 600/301 |
| 2010/0191541 A1* | 7/2010 | Prokoski | 705/2 |
| 2011/0112442 A1* | 5/2011 | Meger et al. | 600/595 |
| 2011/0245732 A1* | 10/2011 | Mravyan et al. | 600/587 |
| 2011/0308019 A1 | 12/2011 | Terawaki et al. | |
| 2013/0283530 A1 | 10/2013 | Main et al. | |

FOREIGN PATENT DOCUMENTS

| | | | |
|---|---|---|---|
| JP | 2009119082 A * | 6/2009 | |
| WO | WO 0100089 A1 * | 1/2001 | |
| WO | WO 2009/102361 A1 | 8/2009 | |
| WO | 2010045741 | 4/2010 | |
| WO | WO 2011/066151 A1 | 6/2011 | |
| WO | 2011091517 | 8/2011 | |
| WO | WO 2011/091517 A1 | 8/2011 | |

OTHER PUBLICATIONS

PCT International Search Report and Written Opinion for PCT/IB2013/001276, Sep. 17, 2013, 7 Pages.
Bayer L., et al., "Rocking synchronizes brain waves during a short nap," Current Biology, 2011, pp. R461-R462, vol. 21, No. 12.
Fronczek, R., et al., "Manipulation of Core Body and Skin Temperature Improves Vigilance and Maintenance of Wakefulness in Narcolepsy," Sleep, 2008, pp. 233-240, vol. 31, No. 2.
Machiel Van Der Loos, H.F. et al., "Development of Sensate and Robotic Bed Technologies for Vital Signs Monitoring and Sleep Quality Improvement," Autonomous Robots, 2003, pp. 67-79, vol. 15.
Malakuti, K., "Towards an Intelligent Bed Sensor: Non-Intrusive Monitoring of Sleep Disturbances via Computer Vision Techniques," Thesis, University of Victoria, 2008, 93 pages.
Raymann, R., et al., "Skin deep: enhanced sleep depth by cutaneous temperature manipulation," Brain, 2008, pp. 500-513, vol. 131.
Yousefi, R. et al., "Bed Posture Classification for Pressure Ulcer Prevention," 2011 Annual International Conference of the IEEE, Engineering in Medicine and Biology Society, EMBC, Aug. 30, 2011-Sep. 3, 2011, pp. 7175-7178.
Yousefi, R. et al., "A Smart Bed Platform for Monitoring & Ulcer Prevention," 2011 4th International Conference on Biomedical Engineering and Informatics (BMEI), IEEE, 2011, pp. 1362-1366.

* cited by examiner

Patient Turn Monitor Primary Functions
1. Turn Tracker
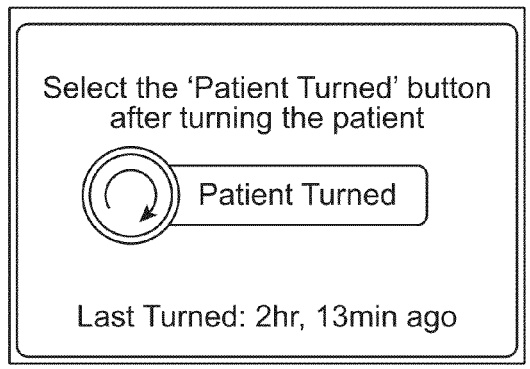
2. Real Time Pressure Monitor    3. Pressure Exposure Monitor
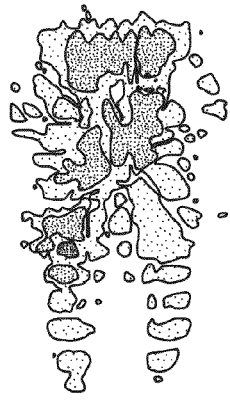 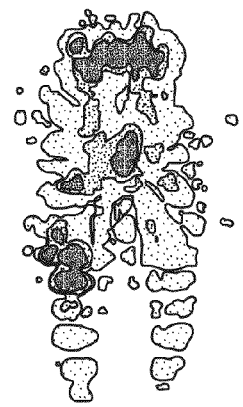
FIG. 1
Mathematical Representation of Pressure Exposure
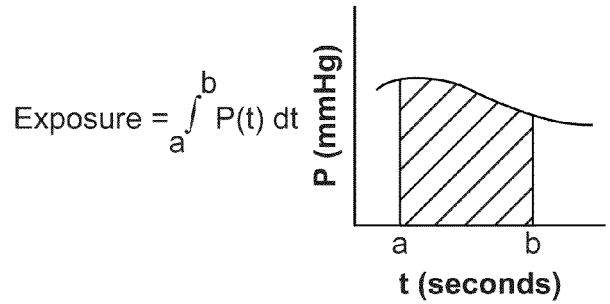
$$\text{Exposure} = \int_a^b P(t)\, dt$$
FIG. 2

Interface Pressure Map of Patient Positions
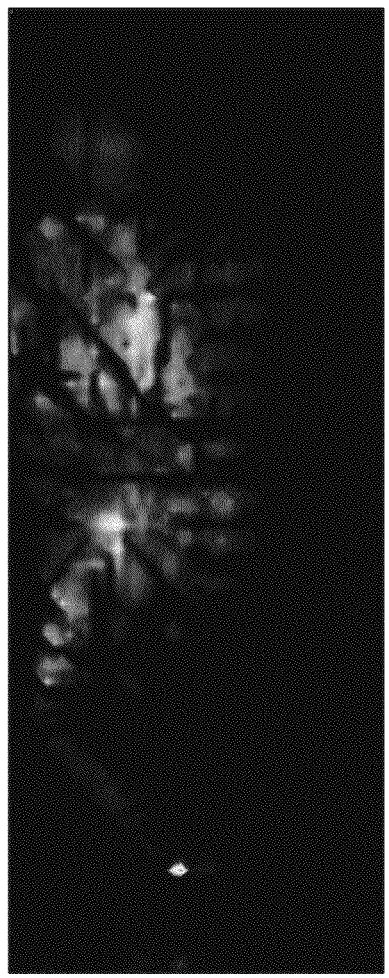 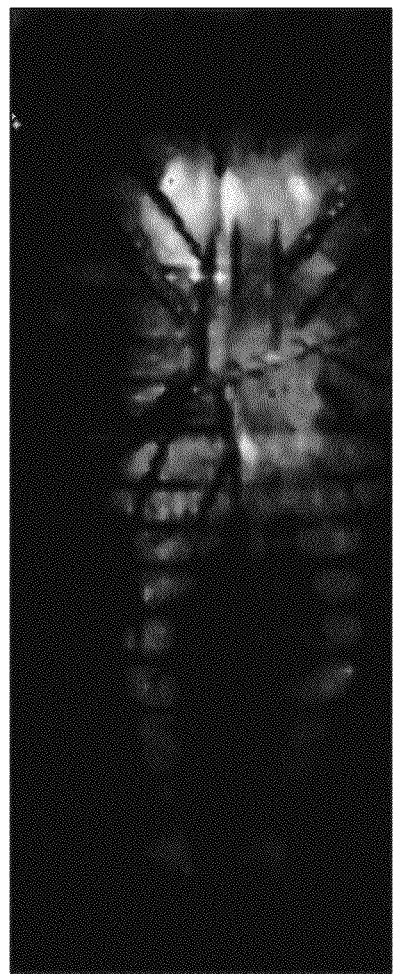
Patient on Right Side          Patient on Back
FIG. 6

Braden Risk Scale™ — Braden Risk Scale - User Interface

| Name | 1 | 2 | 3 | 4 | Score | Description |
|---|---|---|---|---|---|---|
| Sensory Perception | Completely Limited | Very Limited | Slightly Limited | No Impairment | 3 | Nutrition Usual food intake pattern. |
| Moisture | Constantly Moist | Very Moist | Occasional Moist | Rarely Moist | 2 | Very Poor Never eats a complete meal. Rarely eats more than 1/3 of any food offered. Eats 2 servings or less of protein (meat or dairy products) per day. Takes fluids poorly. Does not take a liquid dietary supplement OT is NPO and/or maintained on clear liquids or IV's for more than 5 days. |
| Activity | Bedfast | Chairfast | Walks Occasional | Walks Frequent | 3 | |
| Mobility | Completely Immobile | Very Limited | Slightly Limited | No Limitation | 3 | |
| Nutrition | Very Poor | Probably Inadequate | Adequate | Excellent | 1 | |
| Friction & Shear | Problem | Potential Problem | No Apparent Problem | | 2 | |

Evaluation Interval [4] Hrs.        Total Score: 14 - Moderate Risk

[X] Cancel        [→] Next

FIG. 11

RISK MODELING FOR PRESSURE ULCER FORMATION

FIELD OF THE INVENTION

The present invention is directed to methods and systems for monitoring and assessing risk of pressure ulcer formation.

BACKGROUND

Pressure imaging systems have been used to provide interface pressure information for the assessment of medical support surfaces such as wheelchair seats and hospital beds. The primary goal of performing these surface assessments has been to prevent the development of pressure ulcers.

Pressure ulcers (also known as pressure sores, decubitus ulcers or bed sores) are areas of localized damage to the skin and underlying tissue, generally understood to be caused by pressure, shear or friction. Deep tissue damage can occur under bony prominences and there is a much greater potential for these wounds to deteriorate without treatment since the initial lesion is not visible on inspection of the skin.

Pressure ulcers occur on patients in hospitals as well as in the community. They are commonly found in the elderly and in patients with reduced mobility and poor nutrition. The prevalence of pressure ulcers in hospitals within Canada and the United States ranges from 5-33% and represents a significant burden on quality of life as well as a financial burden on the health care system.

In hospitals, caregivers try to reduce the prevalence of pressure ulcers by manually turning the patient on a regular turning schedule, typically every two hours. This is an attempt to relieve pressure in body areas that have been in contact with the hospital bed for prolonged periods of time. Cushion supports and specialty beds are other tools that can be used to relieve interface pressure. However, the cost of these tools varies widely and their ability to actually reduce the incidence of ulcers is not well understood.

Clinical studies have shown that a consistently executed turning schedule can reduce the incidence of pressure ulcers (DeFloor et al. (2005)). However, in spite of the fact that hospitals typically include turning schedules in their clinical pathway for the prevention of pressure ulcers, the prevalence of hospital acquired pressure ulcers remains high.

Therefore, there is a need in the art for method and system which provides useful and meaningful information regarding pressure sensor information, and that assists clinical staff in more effectively and reliably implementing patient turning protocols.

SUMMARY OF THE INVENTION

The present invention relates to a method and system for modelling pressure exposure and/or the risk of pressure ulcer formation in a meaningful and useful manner and presenting the risk assessment to a user in a novel and informative manner. The method and system may also provide information that increases a caregiver's awareness of the presence of elevated bed pressures, and the effect of long term exposure to pressure in areas of the body that are susceptible to pressure ulcers. Better informed clinical staff may be more confident in their decision to reposition a patient and are more likely to effectively follow a turning schedule.

In one aspect, the invention comprises a method of assessing a patient's exposure to interface pressure, wherein the patient is supported on a support surface and a pressure sensing interface having a plurality of sensels is placed between the patient and the support surface, the method comprising the steps of:

(a) determining a desired turning interval;
(b) calculating a pressure exposure delta, $E\Delta$, for each of a plurality of sensels, based on the measured pressure value, P, multiplied by an interval of time ($E\Delta = P \times \Delta t$);
(c) determining a pressure exposure value, $E(t)$, for each of a plurality of sensels, by accumulating pressure exposure deltas over a pre-determined period of time ($E(t) = \Sigma E\Delta(t)$);
(d) deriving a normalized pressure exposure, $E_{norm}$, from $E(t)$, the selected turning interval and the maximum pressure range of the sensor;
(e) displaying the normalized pressure exposure value for each sensel to a user; and
(f) periodically repeating steps (b) to (e).

In another aspect, the invention comprises a system for determining and displaying pressure exposure values for a patient supported on a support surface, comprising:

(a) a pressure sensing interface having a plurality of sensels placed between the patient and the support surface;
(b) computer-implemented processing means comprising a component for calculating a pressure exposure delta, $E\Delta$, for each of a plurality of sensels based on the measured pressure value, P, multiplied by an interval of time ($E\Delta = P \times \Delta t$); a component for determining a pressure exposure, $E(t)$, for each of a plurality of sensels by accumulating pressure exposure deltas over a chosen period of time ($E(t) = \Sigma E\Delta(t)$); a component for deriving a normalized pressure exposure $E_{norm}$ based on a selected turning interval and a maximum pressure range of the sensor for each of the plurality of sensels; wherein the processing means is operatively connected to the pressure sensing interface; and
(c) a display connected to the processing means for showing the $E_{norm}$ values to a user.

In one embodiment, the processing means further comprises a component for producing a pressure exposure map from the plurality of $E_{norm}$ values, which pressure exposure map is shown on the display.

In another aspect, the invention comprises a method of assessing the risk of a patient developing a pressure ulcer, wherein the patient is supported on a support surface, and a pressure sensing interface having a plurality of sensels is placed between the patient and the support surface, the method comprising the steps of:

(a) obtaining a pressure value from each of a plurality of sensels and deriving a time-to-high risk ($T_{HR}$) value for each sensel from the pressure value;
(b) adjusting the $T_{HR}$ value by considering at least one risk modifier;
(c) converting the risk-adjusted $T_{HR}$ value into a risk delta comprising a change in risk over a unit of time;
(d) adjusting a risk value by the risk delta;
(e) displaying the adjusted risk value to a user; and
(f) periodically repeating steps (a) to (e).

In one embodiment, the $T_{HR}$ value is determined by comparing the pressure value to stored pressure vs. time data which comprises a $T_{HR}$ value for a given pressure value, or by applying a pre-determined mathematical formula to the pressure value.

In another aspect, the invention comprises a risk assessment system for assessing the risk of a patient developing a pressure ulcer, wherein the patient is supported on a support surface, the system comprising:

(a) a pressure sensing interface having a plurality of sensels placed between the patient and the support surface;
(b) an input device for accepting a risk modifier level by considering at least one risk modifier;
(c) computer-implemented processing means comprising a component for determining a pressure value for each of the plurality of sensels and deriving a $T_{HR}$ value for each pressure value, a component for adjusting the $T_{HR}$ value for the risk modifier level, a component for converting the risk-adjusted $T_{HR}$ value into a risk delta comprising the change in risk over a unit of time, and adjusting a risk value by the risk delta, wherein the processing means is operatively connected to the pressure sensing interface and the input device; and
(d) a display connected to the processing means for displaying the adjusted risk value to a user.

The component for determining a $T_{HR}$ value for each of the plurality of sensels may do so by obtaining a pressure value from the sensels and comparing it to stored pressure vs. time data which comprises a $T_{HR}$ value for a given pressure value, or by applying a mathematical formula to the pressure value. The system may further comprise a component for creating a risk map from the risk values for each of the plurality of sensels, which risk map is shown on the display.

In another aspect, the invention may comprise a patient turn management system comprising:
(a) a pressure sensing interface having a plurality of sensels placed between the patient and the support surface and means for producing a pressure interface map;
(b) an input device for indicating when a caregiver has initiated a patient turn or repositioning;
(c) a timer for tracking elapsed time since the last caregiver initiated turn or repositioning; or the remaining time until the next scheduled turn is due;
(d) computer-implemented processing means comprising:
  (i) a component for determining a pressure value for each of the plurality of sensels and deriving a pressure exposure value based on the determined pressure value; wherein the processing means is operatively connected to the pressure sensing interface; or
  (ii) a component for determining a pressure value for each of the plurality of sensels and deriving a $T_{HR}$ value for each pressure value, a component for adjusting the $T_{HR}$ value for the risk modifier level, a component for converting the risk-adjusted $T_{HR}$ value into a risk delta comprising the change in risk over a unit of time, and adjusting a risk value by the risk delta;
  wherein the processing means is operatively connected to the pressure sensing interface and the input device; and
(e) a display connected to the processing means for displaying the pressure exposure values or risk values, the pressure interface map, and the elapsed time since the last caregiver turn or repositioning.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIG. 1 shows representations three functions of one embodiment of the present invention: pressure exposure map, interface pressure map, and elapsed time turn timer with patient turn input button.

FIG. 2 shows a mathematical representation of pressure exposure.

FIG. 6 shows pressure map images of two different body positions.

FIG. 11 is a screen shot of one embodiment of a risk assessment input interface.

DETAILED DESCRIPTION OF PREFERRED EMBODIMENTS

Figure 3:
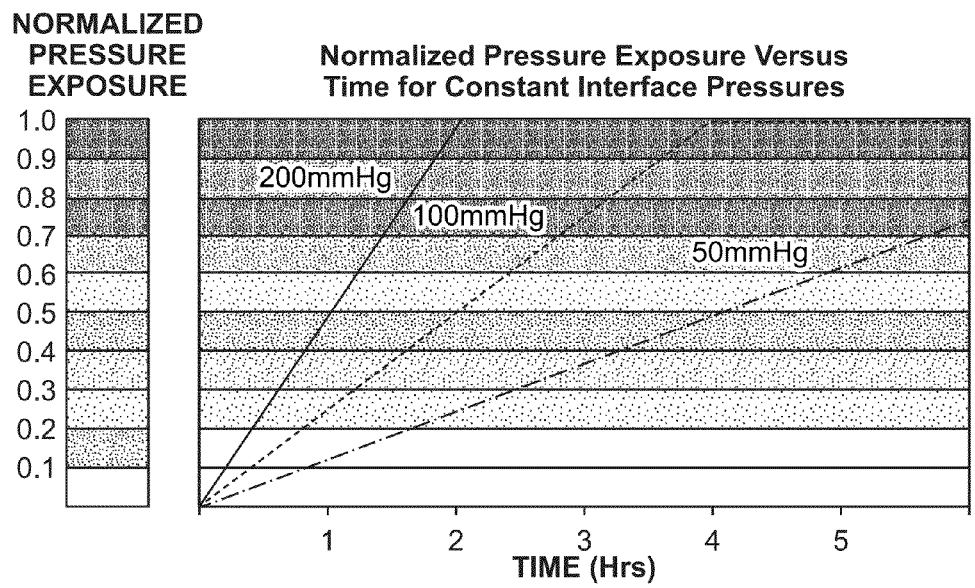
FIG. 3 shows the relationship between pressure, elapsed time, and pressure exposure, including one possible representation of a colour scale applied to normalized pressure exposure.

The invention relates to a system and method for deriving and displaying useful information from real-time pressure measurements, for caregivers or health workers concerned with subjects or patients at risk of forming pressure ulcers. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

In one aspect, the present invention relates to a system and method for tracking a patient's exposure to bed pressure and managing the execution of patient turning or repositioning protocols in a novel informed manner. In one embodiment, the present invention provides a novel method of tracking the measured patient/bed interface pressure over time and providing this information to a user in the form of a pressure exposure map. In one embodiment areas of highest exposure are located using visual indicators overlaid on an interface pressure map. In another embodiment, the present invention provides a system and method of assessing overall pressure ulcer risk by monitoring specific factors and combinations of factors in a novel manner, and presenting the risk assessment to a user in a novel and informative manner. In one embodiment, the risk assessment is presented as a risk map which allows a user to visually determine areas of high and low risk.

In one embodiment, areas of highest risk are located using visual indicators overlaid on the interface pressure map.

Embodiments of the present invention also provide a system and method of managing patient turning protocols using the pressure exposure or risk assessment information provided.

By providing continuous, patient-specific risk information, either or both of the pressure exposure map and the risk map can assist a caregiver in making more informed choices regarding the repositioning of the patient for the prevention of pressure ulcers.

In one embodiment, pressure exposure over time is presented as a pressure exposure map which allows a user to visually identify body areas with higher or lower exposure to pressure, based on the measured pressures and the time that the patient is exposed to these pressures.

Pressure Exposure Management

In another embodiment, pressure exposure, interface pressure, and patient turn tracking information is used to improve the quality and consistency of patient turn management by providing continuous feedback to the caregiver. A representation of these three functions is shown schematically in FIG. 1.

A pressure exposure map of the present invention utilizes real-time interface pressure inputs to track and accumulate pressure exposure over time. The interface pressure inputs are obtained by pressure sensors associated with the patient support surface, which report the pressure exerted between the support surface and the patient. A pressure sensor mat which provides a plurality of sensels, typically arranged in a 2-dimensional grid, may be used. A sensel is an individual pressure sensor within the overall array of sensors. Such mats are well-known in the art and commercially available. The determination of pressure exposure is processed over a plurality of locations, and over time, and may be combined with or determined independently of any risk factors described herein.

Pressure exposure is a quantification of the body/support surface interface pressure that the patient is subjected to over a period of time. Conceptually, this is similar to sun exposure, radiation exposure, or a sport diver's exposure to pressure based on the time spent at various depths. Mathematically, pressure exposure is calculated as shown in FIG. 2. The unit of measure for pressure exposure is a standard unit of pressure multiplied by a standard unit of time, such as mmHg(s), psi(s) Kpa(s), or $N/m^2(s)$.

Pressure exposure over a given period of time is calculated by summing pressure deltas, which are calculated by multiplying the measured interface pressure by the elapsed time since the last pressure measurement (Pressure exposure delta, $E\Delta = P \times \Delta t$). The pressure exposure value is determined based on an accumulation of pressure exposure deltas over a defined period of time, $E(t) = \Sigma E\Delta(t)$.

In one embodiment, the absolute pressure exposure is normalized with reference to the scheduled turn interval and the calibration limit of the sensor, $E_{norm} = E(t)/t_{turn\ interval}/P_{max}$. For example, based on a 2 hour turn interval and a maximum calibration pressure of 200 mm Hg, the normalized pressure exposure will reach a maximum value after 2 hours if the measured pressure is a constant 200 mm Hg. Table 1 provides examples of normalized pressure exposure ($E_{norm}$) values based on a maximum sensor calibration limit of 200 mm Hg, where the maximum $E_{norm} = 1$.

TABLE 1.0

Max Pressure Exposure Values Based on Turning Interval

| Turning Interval (seconds) | Maximum E(t) for 200 mmHg limit (mmHg · s) | $E_{norm}$ |
|---|---|---|
| 3600 (1 Hr) | 720000 | 1 |
| 7200 (2 Hrs) | 1440000 | 1 |
| 10800 (3 Hrs) | 2160000 | 1 |
| 14400 (4 Hrs) | 2880000 | 1 |

$E(t)$ and $E_{norm}$ are calculated for each sensel in the pressure sensing grid.

In another embodiment, the normalized pressure exposure value is based on other time or pressure reference values. Based on clinical data or specific user requirements, a lower pressure can be used as a reference value for the purpose of normalizing pressure exposure. Similarly, time periods other than the recommended turning interval can be used. By adjusting the time and pressure reference values, the system can potentially be optimized for different patient types or different patient environments.

The normalized pressure exposure, $E_{norm}$, will accumulate towards a maximum value, which is in one embodiment, $E_{norm} = 1$. At the maximum reference pressure, a value of one is reached once the turning interval time has elapsed. At pressures lower than the maximum reference pressure, $E_{norm}$ does not reach 1 during the turning interval time, but will continue to accumulate, up to the maximum value. $E_{norm}$ will not decrease until pressure has been relieved or until the caregiver has provided input that the patient has been turned or repositioned. FIG. 3 illustrates the accumulation of normalized pressure exposure based on a 2 hour turning interval and maximum sensor pressure limit of 200 mmHg. $E_{normalized}$ values are plotted for constant measured pressures of 200 mmHg, 100 mmHg, and 50 mmHg.

In one embodiment, the normalized pressure exposure, $E_{norm}$, shall continue to accumulate beyond a maximum value of 1. This allows for the location of sensels with the highest accumulated $E_{norm}$. $E_{norm}$ will continue to increase until pressure has been relieved or until the caregiver has provided input that the patient has been turned or repositioned.

In one embodiment, the normalized pressure exposure may be presented as a pressure exposure map. The pressure exposure map is a two dimensional representation of the normalized pressure exposure, absolute pressure exposure, or other value based on the accumulation of pressure measurements over time, obtained from the sensel grid placed between the patient and the support surface.

In one embodiment, areas of highest pressure exposure are highlighted on the pressure exposure map, or two dimensional interface pressure map, using a visual marker such as a color, a ring, arrow, pointer, or other geometric identifier. The visual markers may also provide additional call out information including but not limited to: pressure exposure, normalized pressure exposure, average pressure, peak pressure, time duration of pressure exposure, time duration at current pressure, or time duration at peak pressure. The call out information can be presented by textual or graphical means. In one embodiment, the pressure exposure map may be three-dimensional, with areas of high pressure exposure displayed as peaks with heights proportional to the pressure exposure value.

By providing continuous, patient-specific pressure exposure information, the pressure exposure map can assist a caregiver in making more informed choices regarding where to look for the physical signs of pressure ulcer development and how to best reposition the patient to relieve pressure in the areas with highest pressure exposure. In one embodiment the pressure exposure information can be used to provide an indication of the patient's level of mobility as a mobile patient is less likely to accumulate higher levels of pressure exposure. Mobility information can be presented by textual or graphical means.

After locating areas of high pressure exposure, a caregiver can verify that pressure exposure has been appropriately relieved from a specific area on the patient's body, by referring to the real time pressure image.

In one embodiment, the pressure exposure tracking process of the present invention translates physical inputs (such as interface pressure and duration of interface pressure) into a value that is used to identify where the patient has been exposed to the highest pressures for the longest duration. The sensitivity of the pressure exposure tracking is adjusted based on the patient turn interval implemented by the clinical institution (e.g. every 2 hours) or by other modifiers such as known clinical risk scales, or other physical information such as temperature, moisture, or shear force, which may be acquired by additional sensors or manually. By adjusting the turn interval, or applying other modifiers, the pressure exposure value will accumulate slower or faster. For example, a patient who is completely immobile and at very high risk of developing a pressure ulcer, the turning interval can be reduced to one hour. In this case, higher levels of normalized pressure exposure will be achieved more quickly. Table 2.0 provides an example of normalized pressure exposure accumulation for a sample pressure profile based on turning intervals of 1 hour and 2 hours. (As with previous examples $E_{norm}$ is based on a sensor pressure limit of 200 mmHg.)

TABLE 2.0

Comparison of Pressure Exposure based on 2 Hr and 1 Hr Turning Intervals

| Interval | P (mmHg) | Δt (s) | Accumulated Time (s) | 2 Hr Interval $E_{normalized}$ | 1 Hr Interval $E_{normalized}$ |
|---|---|---|---|---|---|
| 1 | 60 | 900 | 900 | 0.038 | 0.075 |
| 2 | 60 | 900 | 1800 | 0.075 | 0.150 |
| 3 | 100 | 900 | 2700 | 0.138 | 0.275 |
| 4 | 150 | 900 | 3600 | 0.231 | 0.463 |
| 5 | 50 | 900 | 4500 | 0.263 | 0.525 |
| 6 | 50 | 900 | 5400 | 0.294 | 0.588 |
| 7 | 120 | 900 | 6300 | 0.369 | 0.738 |
| 8 | 200 | 900 | 7200 | 0.494 | 0.988 |
| 9 | 180 | 900 | 8100 | 0.606 | 1.213 |
| 10 | 90 | 900 | 9000 | 0.663 | 1.325 |

In addition to the bed surface sensor, in one embodiment, specialized sensors may be placed in pillows and other pressure relieving support surfaces to provide auxiliary support surface interface pressure information. These auxiliary sensors would be monitored in the same way as the main bed sensor.

When the interface pressure falls below a minimum pressure threshold, the normalized pressure exposure value will begin to decrease. The minimum pressure threshold may be chosen over a range of pressure values. For example, there is clinical data that suggests a capillary pressure of 30 mm Hg may be sufficient pressure relief to reduce the risk of tissue breakdown. In one embodiment, minimum pressure thresholds can be set by the user at any value between 30 mm Hg to the minimum value in the sensor's calibration range, which may be 5 mm Hg. In one embodiment, the minimum pressure value is fixed at a clinically accepted level, such as 20 mmHg.

A recent study (Makhous et al (2007)) proposed that for full tissue perfusion recovery the interface pressure should be relieved and relief maintained for a recovery period of 200 to 300 seconds. In one embodiment, the recovery period may be any length of time between 3 minutes minimum up to 20 minutes maximum. In one embodiment, the recovery period is fixed at a clinically accepted level such as 300 seconds.

In one embodiment the pressure exposure value, or normalized pressure exposure value, will be reduced at such a rate that the value will reach zero after the selected recovery period has elapsed. The length of the recovery period chosen determines the magnitude of the negative pressure exposure delta. In one embodiment, this process may be implemented using the following logic statement:
Where:

```
interface_pressure = IP
normalized_pressure_exposure = NEP
stored_normalized_pressure_exposure = SNEP (value is stored
  as NEP accumulates)
minimum_pressure_threshold = selected capillary or relief
  pressure (eg. 20mmHg)
recovery_period = selected recovery period (eg. 10 mins)
max_pressure = max pressure in sensor calibration range (eg.
  200mmHg)
turn_interval = scheduled turn interval (eg. 2Hrs)
Δt = elapsed time used to calculate pressure exposure delta
IF ( IP < minimum_pressure_threshold ) THEN
    IF NEP <> 0 THEN
        NEP = NEP − (SNEP / recovery_period) x Δt
    END IF
ELSE
    NEP = NEP + (IP / max_pressure) x (Δt / turn_interval)
    SNEP = NEP
END IF
```

In one embodiment, the pressure exposure map and system comprises a reset mechanism which resets the pressure exposure values to zero for all sensels. A user may utilize the reset mechanism, for example, if the patient is completely repositioned, such as being rolled over completely. In one embodiment, an input button is the reset mechanism that, when pressed, resets the pressure exposure map to zero for all sensels.

Figure 7:
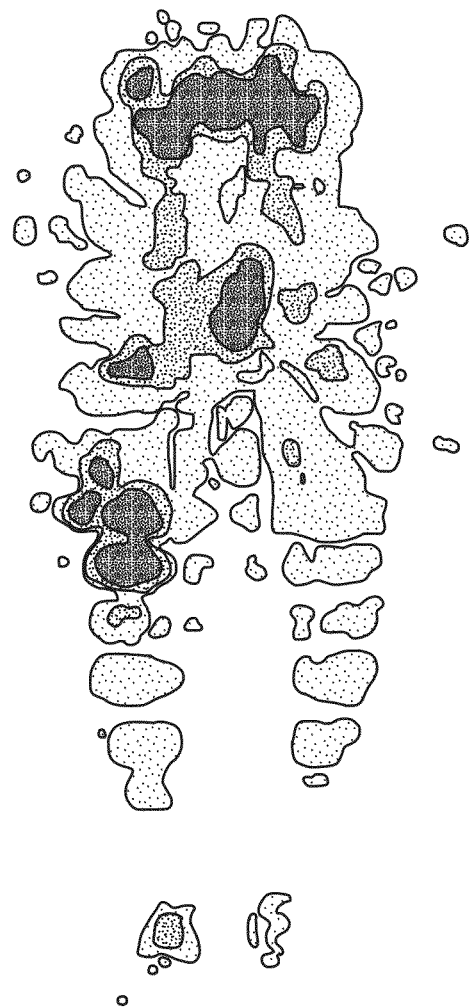
FIG. 7 shows one exemplary representation of the pressure exposure map.

In one embodiment, the pressure exposure values from a plurality of sensels results in a pressure exposure map that is a graphical representation of the pressure exposure on a patient's body. The system displays the normalized pressure exposure values for all sensels in the form of a pressure exposure map. The pressure exposure map provides an indication of the location and level of pressure exposure over the patient's body. In one embodiment, if the pressure exposure level in a certain area exceeds a certain level, it may be highlighted, or otherwise modified to catch the attention of a caregiver. As shown for example in FIG. 7, the pressure exposure monitor indicates that the patient has experienced the greatest pressure for the longest period of time in the area of the right buttock, as indicated by the highest colour in the colour scale (red for example). Orange and yellow coloration indicate other areas of significant pressure exposure. Grey coloration indicates low pressure exposure areas. Areas with no coloration do not have significant interface pressure (below 5 mmHg for example) and are typically bed surface areas not in contact with the patient.

In one embodiment a real-time interface pressure map is also available to identify body areas with highest interface pressure. This is different from pressure exposure in that it is instantaneous and provides no indication of the duration of the interface pressure. The interface pressure map facilitates a workflow whereby new patient positions can be validated. The workflow may be iterative, where repositioning is validated to ensure new high interface pressure points have not been created, and further repositioning is performed if required.

In one aspect, the invention may comprise a method of adjusting the patient position in response to a high pressure exposure value or group of pressure exposure values exceeding a pre-determined threshold. The method of adjustment may be executed manually by a caregiver, or automatically by system actuated devices.

Risk Map

In another embodiment, the real-time pressure measurements may be converted into a risk assessment and displayed as a risk map, which is analogous to the pressure exposure map described above. A risk map of the present invention is created by a risk algorithm which utilizes physical factor inputs and physiological factor inputs to assign a risk level, by comparing the input data with stored data which correlates input values with pre-defined risk levels. The physical factor and physiological factor inputs are obtained by sensors or by user observation or determination and input, or a combination of sensors and direct user input. The determination of risk level is processed over a plurality of locations, and over time.

The key physical risk factor is interface pressure. Obviously, increased pressure results in reduction or cessation of soft tissue perfusion. Time is also an important factor as the longer the increased pressure bears on the soft tissue, the greater the potential for the development of pressure ulcers. The interface pressure sensor utilizes an array of capacitive pressure sensing elements to create a pressure map of the patient/support surface interface. In one embodiment, pressure is measured over the range of 5 mm Hg to 200 mm Hg.

Other key risk factors for pressure ulcer formation include physical and physiological factors. Physical factors include:

Moisture/Incontinence
   Alters the skin's natural barrier protection and increases the potential for skin breakdown Temperature
   High skin temperatures result in perspiration and increases risk factors due to moisture.
   Low skin temperatures result in poor circulation.

Shear
   Increases strain on tissue and can result in reduced circulation.

Physiological factors may include:

Age
   Elderly people are at higher risk for the development of pressure ulcers due to skin changes, slower metabolism, poorer nutrition and hydration, and compromised respiratory function.
   Elderly people are also at higher risk of chronic health conditions such as circulatory problems and diabetes.

Mobility
   Mobility reduces the risk of developing pressure ulcers as pressure is frequently relieved in areas that may be at risk
   The exception is shear and friction that can result from excessive movement and contribute to skin breakdown.

Disease
   Diseases such as Peripheral Vascular Disease (PVD) can cause acute or chronic ischemia that results in a lack of blood supply to at risk tissues.
   Similarly, heart and lung disease can restrict blood or oxygen supply to at risk tissues.

Surgery
   Surgery often restricts the movement of the patient either during surgery or post-op and exposes the patient to longer term pressure points that have greater risk of causing pressure ulcers.
   During recovery it can be more difficult the re-position a patient that is connected to monitoring equipment.

Circulation
   Poor blood circulation results in inadequate delivery of oxygen, nutrients and blood cells to the tissue cells and therefore increases risk of breakdown.

Diabetes
   Poor blood circulation.
   People with diabetes can have very poor circulation in the arms and legs in particular. Diabetes is often listed as a separate risk factor for tissue breakdown.

Nutrition
   Vitamin & protein deficiencies increase risk of tissue breakdown.
   National Pressure Ulcer Long-term Care Study (NPULS) associated involuntary weight loss with a 74% increase in risk of developing pressure ulcers.

Dehydration
   NPULS associated dehydration with a 42% increase in risk of developing pressure ulcers.

Obesity
   Poor blood flow in fatty tissues.
   Fatty tissues tend to compress more than muscle tissue.
   Reduced mobility.

The number of risk factors and their inter-relationship make it difficult to perform an assessment on a patient that takes all factors into consideration. There are risk assessment tools that attempt to address the most critical factors to predict a patient's level of risk. Patients that are assessed with a higher level of risk are candidates for a higher level of preventative care, including, more frequent turning schedules and skin inspection, special support surfaces, friction reducing creams and massage in the areas of high risk.

For example, the Braden Scale uses six categories where patients are assessed and rated on a scale of 1 to 4. The lower the overall score the greater the risk of developing pressure ulcers. The categories are:

Sensory Perception
   Moisture
   Activity
   Mobility
   Nutrition
   Friction & Shear The Waterlow prevention/treatment policy uses a scoring scheme that is based on six categories plus three additional "special risks" categories. The higher the overall score the greater the risk of developing pressure ulcers. The six main categories are Body type and weight
   Skin condition
   Sex and Age
   Nutrition
   Continence
   Mobility The three "special risks" categories are:
   Tissue malnutrition
   Neurological deficit
   Major surgery or trauma The Norton Scale uses five categories where patients are assessed and rated on a scale of 1 to 4. The lower the overall score the greater the risk of developing pressure ulcers. The categories are:

General physical condition
Mental state
Activity
Mobility
Incontinence

Additional risk assessment scales include the modified Norton risk scale, the Glamorgan pediatric risk scale, and the Risk Assessment Pressure Sore (RAPS) scale. The modified Norton scale adds some additional categories to the traditional Norton scale. The RAPS scale utilizes some categories taken from the modified Norton scale, Braden scale and adds three new categories derived from research results. The Glamorgan risk scale was developed more recently and focuses on pressure ulcer risk for children.

Figure 10:
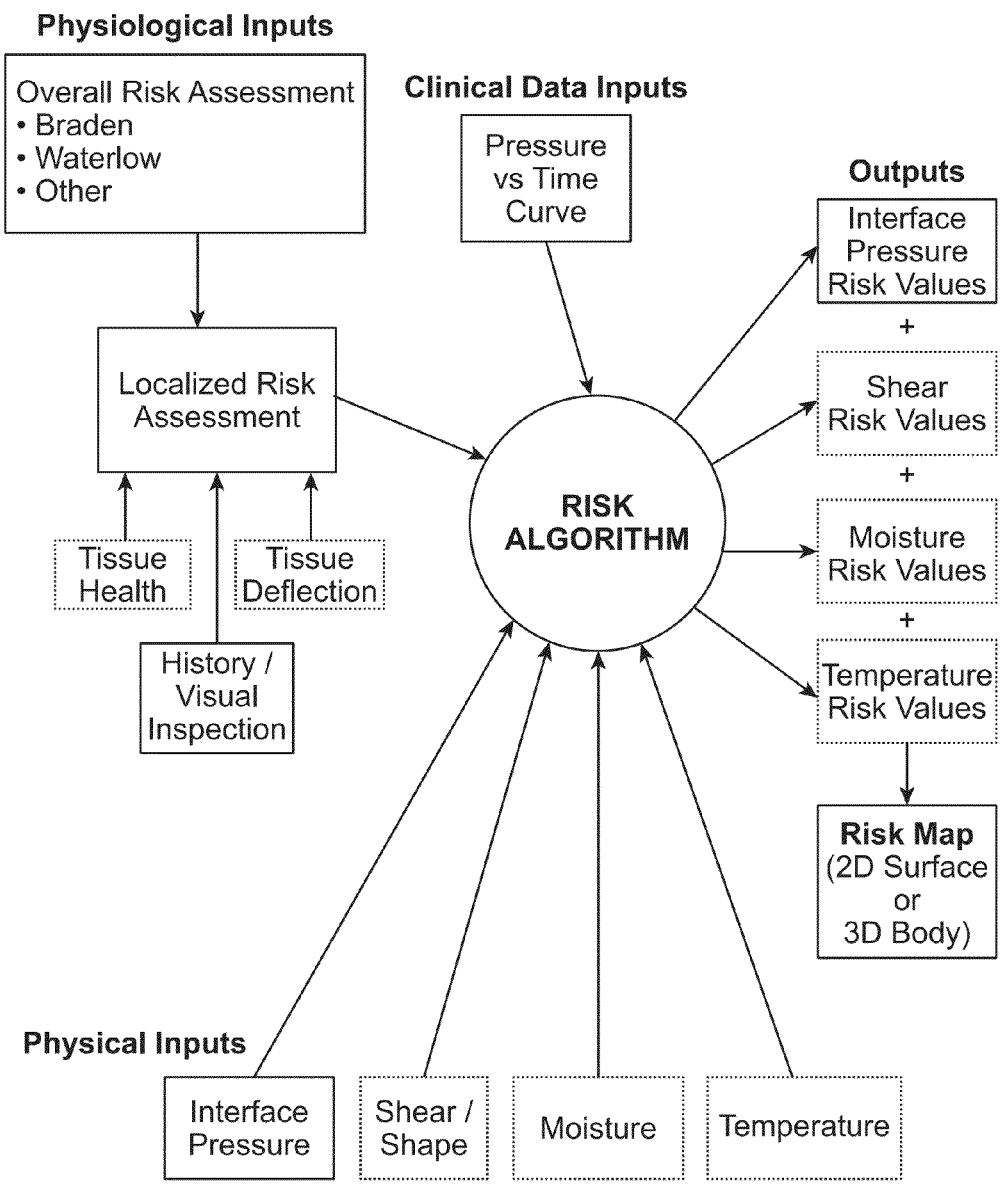
FIG. 10 shows a schematic representation of one embodiment of a risk algorithm of the present invention.

In one embodiment, the risk modeling process of the present invention translates physical inputs (such as interface pressure and duration of interface pressure) into a risk value that is used to identify when the patient is at risk of developing a pressure ulcer. The sensitivity of the risk model is adjusted based on physiological factors that are captured through risk scale assessment, patient specific physiology, and the caregiver's own assessment of the patient. The risk model uses this information to calculate risk values that can be mapped onto the patient's body where it contacts the support surface. This biometric risk information can then be used by caregivers to monitor and assess a patient's level of risk in specific areas of the body. FIG. 10 provides a block diagram of the risk model concept of the present invention.

Figure 8:
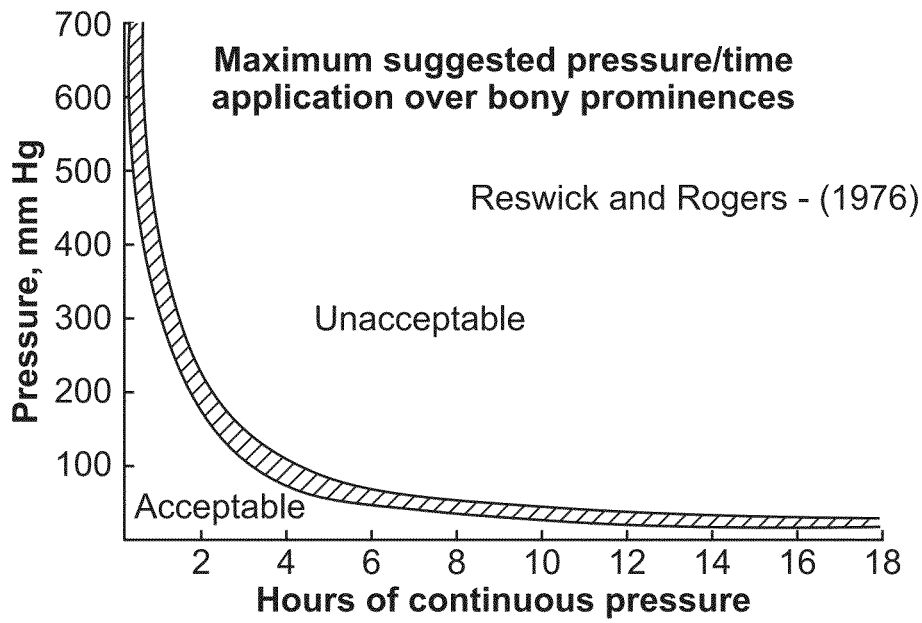
FIG. 8 (prior art) shows a clinically derived pressure vs. time graph known in the literature.

The primary clinical data input into the risk model comprises a pressure v. time curve such as Reswick & Rogers (1976) or Linder-Ganz et al (2006) as the basis for calculating the risk of tissue breakdown. Reswick and Rogers (1976) formulated tissue tolerance guidelines based on clinical data and the results of their study were summarized in a pressure v. time curve that highlighted the threshold where pressure ulcers where likely to develop. The Reswick and Rogers pressure v. time curve is shown in FIG. 8.

These curves indicate that there is a direct relationship between the magnitude of interface pressure, the hours of continuous pressure, and the risk of developing a pressure ulcer. Other curves may be utilized, including those derived in other studies (Patterson and Fisher 1986, Peters et al 2005, Gefen et al 2008) or other customized or proprietary pressure v. time curves. Proprietary pressure v. times curves may be obtained through independent clinical studies or research into biometric feedback such as a seating comfort study. The Linder-Ganz curve is different from the Reswick and Rogers curve at the high and low ends of the pressure curve. The Linder-Ganz curve is compared against the Reswick and Rogers curve in FIG. 9.

Figure 9:
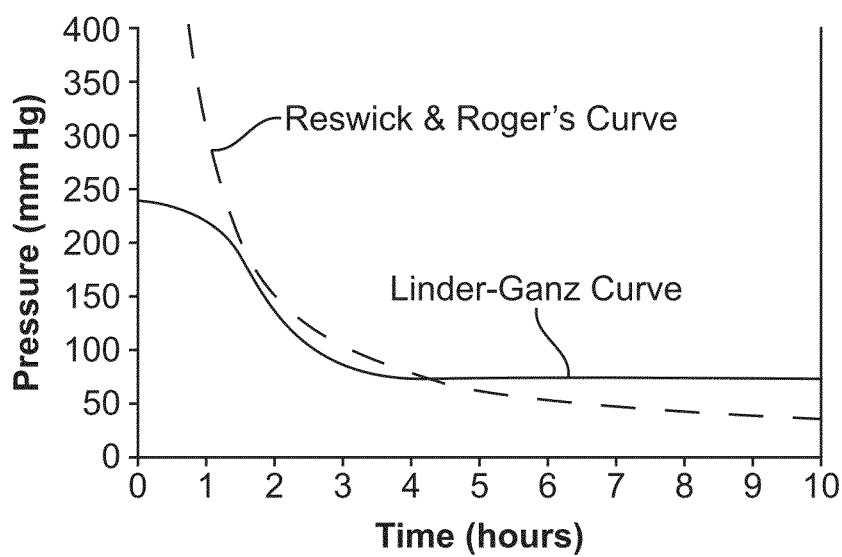
FIG. 9 (prior art) shows another clinically derived pressure vs. time graph known in the literature.

For example, based on the pressure v. time curve shown in FIG. 9, an interface pressure of approximately 160 mmHg is acceptable for just under two hours. If the pressure is not relieved within this time frame, then the patient is at high risk of developing a pressure ulcer. Table 1 details the high risk time intervals for various pressures based on the Linder Ganz et al (2006) curve.

TABLE 1

| Pressure v. Time Data based on Linder Ganz et al (2006) | | |
|---|---|---|
| Interface Pressure | Time to Accumulate High Risk | |
| (mmHg) | Time (hrs) | Time (mins) |
| 233 | 0.33 | 20 |
| 231 | 0.5 | 30 |
| 218 | 1.083 | 65 |
| 201 | 1.33 | 80 |
| 181 | 1.58 | 95 |
| 164 | 1.75 | 105 |
| 141 | 2 | 120 |
| 122 | 2.25 | 135 |
| 100 | 2.58 | 155 |
| 80 | 3.67 | 190 |
| 70 | 3.83 | 230 |

The time-to-high risk based on interface pressure shall be referred to herein as $T_{HR}$ and is defined as an estimate of the duration of time a patient can be exposed to the pressure currently being experienced before a pressure ulcer may begin to form. For example, the Linder-Ganz et al (2006) study concludes that pressures in excess of 240 mmHg can cause pressure ulcers in as little as 15 minutes to 1 hour. Thus, in one embodiment, a conservative estimate of 20 minutes as the $T_{HR}$ is applied to a pressure of 233 mmHg (based on the Linder-Ganz curve in FIG. 9).

The risk model calculates a $T_{HR}$ value based on a pressure v. time curve for every sensor in the sensor array, which may be of any size. In one embodiment, the sensor comprises 50×125 (6250) sensors. The $T_{HR}$ value may be derived from a look-up table or by using a mathematical function that is fit to the chosen pressure v. time curve.

Although the invention has been exemplified using known clinical data of pressure v. time relationships, it is not limited to the clinical data presented in the literature cited above or presented in the Figures and Tables herein. As new clinical data becomes available the pressure v. time curve used in the risk model can be modified to reflect better models for predicting tissue breakdown. Field data acquired by the use of the present invention could also be used to develop alternative pressure v. time curves.

Risk Adjustment

After the risk scale assessment is complete, the patient is assigned the risk level determined by the patient's skin condition or based on patient history. In one embodiment, risk levels are adjusted based on the clinician's input for Braden Assessment and Skin Condition or the Waterlow scale, is also provided as an input into the risk algorithm. FIG. 11 illustrates one possible user interface for entering a Braden Risk scale assessment.

Once the user completes the risk assessment the patient is assigned a score that translates to risk level. In one embodiment, three risk levels (Low, Medium and High) are used. The sensitivity of the risk model is then adjusted based on the assigned risk level. Table 3 illustrates the relationship between Braden Risk Level and the $T_{HR}$ in one embodiment. Based on the Braden Risk level, the $T_{HR}$ value is reduced by a corresponding safety factor. In one embodiment, the $T_{HR}$ value is reduced by 25% for Moderate risk and 50% for High risk, as shown in Table 3. More risk levels may be used if more granularity is required in the risk model adjustment.

TABLE 3

Effect of Braden Risk Level on Pressure v. Time Curve

| Braden Risk Level | Pressure Versus Time Curve |
|---|---|
| Low | Baseline pressure versus time curve (such as unmodified Linder-Ganz) |
| Medium | Reduce $T_{HR}$ by 25% (Linder-Ganz curve shown in FIG. 9 shifts to the left) |
| High | Reduce $T_{HR}$ by 50% (Linder-Ganz curve shown in FIG. 9 shifts to the left) |

As an example, a patient with "low risk" might have an area on their body where the interface pressure is measured to be 141 mmHg. Based on Table 1, the risk model would assign this area a $T_{HR}$ value of two hours. If the same patient where rated as "high risk" then the risk model would assign this area the maximum risk value after only 50% of the $T_{HR}$, or in this case one hour.

In this manner, other risk assessment scales can be incorporated into the risk model in addition or in the alternative. In addition, data from more recent clinical studies can be incorporated as proprietary risk factors. New risk factors or new combinations, relative weightings of risk factors (such as age, sex, recent weight loss, muscle deterioration, or obesity) could be used as part of an alternative risk scale.

Figure 14:
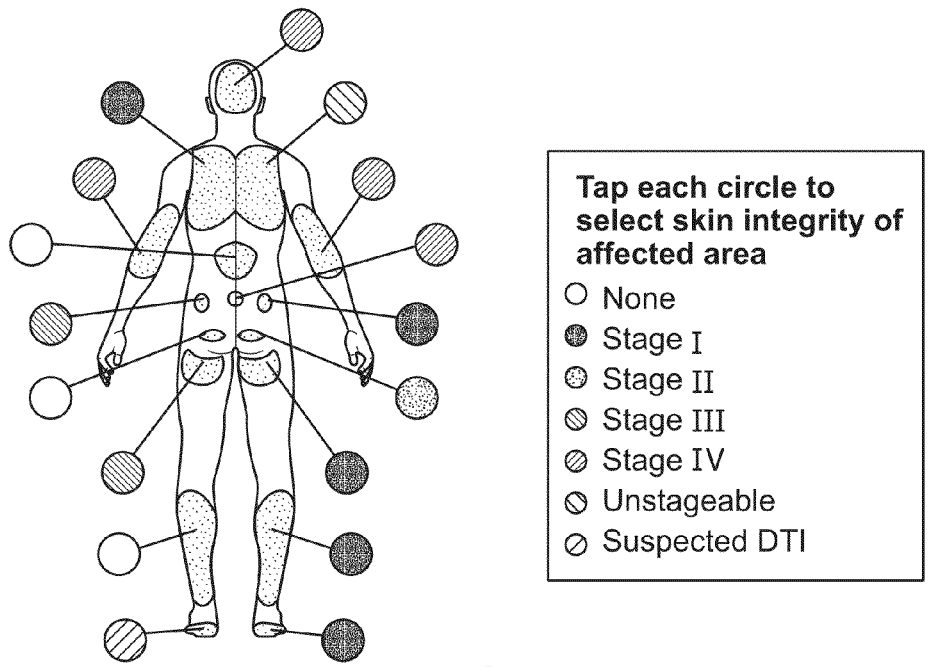
FIG. 14 is a screen shot of one embodiment of a risk adjustment input interface.

Preferably, different anatomical zones are assigned different risk levels. A patient with a previous history or early signs of pressure ulceration in the sacrum area could have the risk level increased in the "Hips" body zone or more specifically for the sacrum body area. This will increase the sensitivity of the risk model for the relevant body zone. FIG. 14 illustrates one embodiment of a user interface for adjusting the risk level for body areas. An alternative Skin Condition interface would allow selection of specific body areas using a 3D body image.

Tissue Deformation

Recent studies have proposed that there is a relationship between the relative deformation of a tissue and the risk of breakdown of that tissue, Gefen (2009). Thus, in one embodiment, the potential for a patient's tissue to deform around bony prominences could be measured as part of the risk assessment process. The deformation of a patient's tissue could be measured using an indenter device that measures the amount of indentation when a known force is applied to the tissue. Alternatively, the elasticity of the tissue could be measured using vibro-elastography. Tissue deformation or elasticity data is then applied to adjust the risk level for a body zone. More detailed machine vision would be even more effective because the risk level could be adjusted for areas around the bony prominences based on the tissue deformation characteristics.

Tissue Health

Deep tissue injuries may be used as part of the risk assessment process. For example, a non-invasive sensor capable of measuring multiple deep tissue characteristics, such as blood flow and oxygenation, would permit the assessment of risk areas on the patient. Testing could be done as part of the risk assessment process to determine if areas around the bony prominences shows signs of pre-existing poor tissue health. The risk level assigned to corresponding body zones could be elevated to increase the sensitivity of the risk model in these areas.

Other Sensor Data

In one embodiment, the risk model uses sensor data to calculate a risk value. The primary input is interface pressure but other important risk factors may also be monitored and have an impact on the calculated risk value. For example, moisture is a known contributor to the risk of developing pressure ulcers. A moisture sensor would allow the assigned risk level to be automatically increased in the event that moisture was detected at the patient/support surface interface. Similarly, temperature and shear could also be used to adjust the sensitivity of the risk model.

In addition to the bed surface sensor, in one embodiment, specialized sensors may be placed in pillows and other pressure relieving support surfaces to provide auxiliary support surface interface pressure information. These auxiliary sensors would be monitored in the same way as the main bed sensor. Each auxiliary sensor would have a risk level assigned to it and a risk value would be calculated for each of its individual sensors based on the same pressure vs time curve used by the main bed sensor.

Shear

In one embodiment, one or more shear sensors are used to create a shear map of the patient/support surface interface. A shear sensor tracks the displacement of two conductive elements in the direction of the applied shear force. An elastomer or piezoelectric material is bonded between the two conductors and provides an elastic force corresponding to the displacement due to shear. This allows the shear force to be calculated based on the displacement of the conductive elements. The greater the shear force the greater the risk of tissue breakdown. A risk value for each shear sensor is calculated based on the intensity of the shear force.

Moisture

In one embodiment, one or more moisture sensors detect the presence of moisture on the support surface. It provides a simple YES/NO status to indicate if more than a negligible amount of moisture has been detected. A single sensor can provide moisture status for the entire support surface or moisture information can be more localized by using multiple moisture sensors on a surface. The moisture sensor uses strips of conductive fabric adhered to an absorbent sheet to detect the presence of bodily fluids on the sensor surface. A minimum of two conductive strips are required. The moisture sensor monitors the two conductive strips to determine when the impedance between the conductors has reduced below a threshold level. A saline solution (bodily fluid) absorbed into the cotton between the two conductive fabric strips will conduct electricity between the two fabric strips and therefore the impedance between the fabric strips will decrease as the conductivity increases. An impedance below the threshold level indicates the presence of sufficient moisture to cause the risk of developing a pressure ulcer to increase.

Multiple strips of conductive fabric can be used in a grid arrangement to further locate the area on the patient support surface where moisture has been detected. The moisture detection and location information is communicated from the sensor to the application software using a standard serial communication protocol such as USB.

Temperature

The temperature sensor utilizes an array of temperature sensing elements to create a temperature map of the patient/support surface interface. Temperatures above or below normal body temperature can elevate the risk of pressure ulcers. A risk value for each temperature sensor is calculated based on the temperature deviation from normal. Higher temperatures can also be assigned a greater risk factor than lower temperatures.

Body Zones

Figure 12:
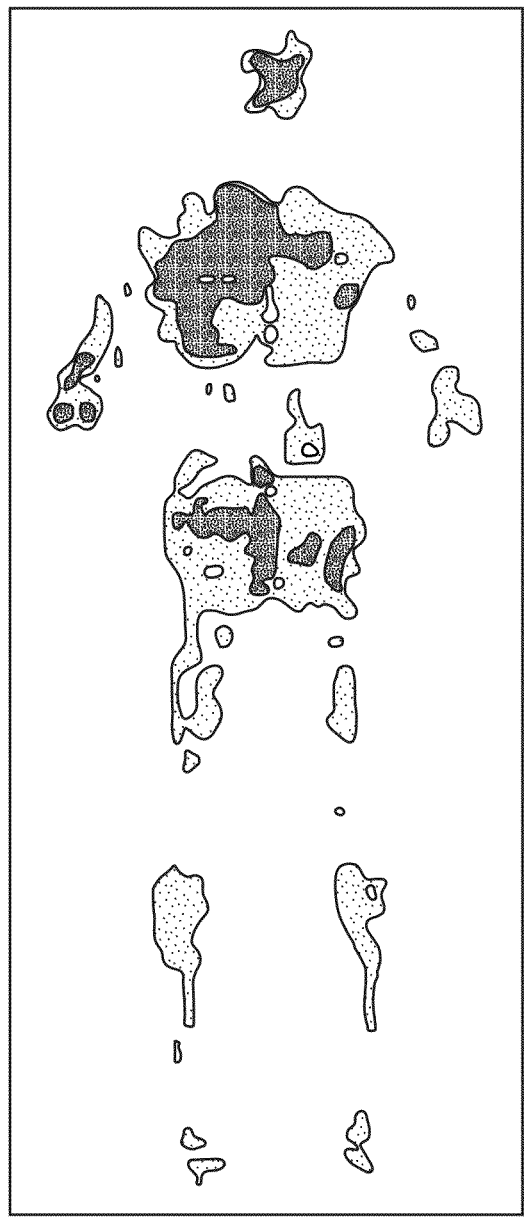
FIG. 12 is a screen shot of one embodiment of a pressure map.
Figure 13:
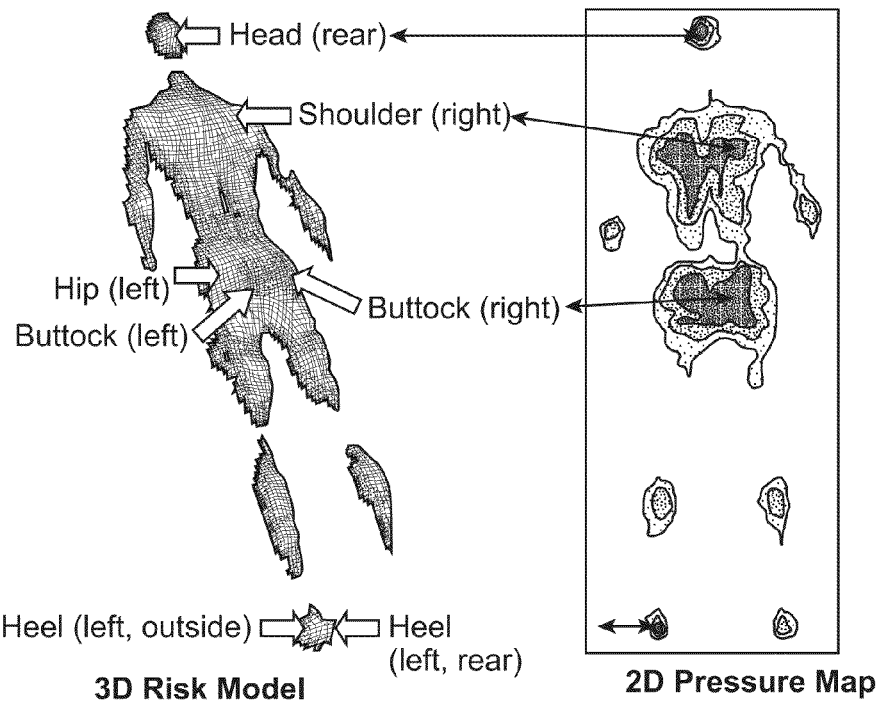
FIG. 13 shows a three-dimensional risk model derived from a two-dimensional pressure map through machine vision.

In one embodiment of the present invention, a pressure sensor or a group of pressure sensors may be correlated to a specific locations on the body, either manually, or by machine processing (machine vision). The two-dimensional interface pressure map may be processed to determine body zones, which may be used to visualize or analyze the pressure exposure map, or the risk map. In one embodiment, where a pressure sensor array receives interface pressure inputs from a support surface with a human body resting on it, the application software creates a pressure map which corresponds to a body image as shown in FIGS. 12 and 13. The machine vision component recognizes anatomical patterns of a human body, and can thus correctly assign anatomical labels to features apparent on a two-dimensional interface pressure map. The anatomical feature is then assigned to the sensor, or group of sensors, until the patient is repositioned. In one embodiment, the machine vision component is capable of identifying if the patient is on their side, back or front. For example, based on the position of the patient, a group of sensors can be assigned to the "left heel bottom", "left heel top", "left heel outside", or "left heel inside". By identifying the anatomical feature, the machine vision process allows the risk model to adjust risk based on body location. For example, if skin redness is observed in the "left heel outside" area then the risk for this body area can be elevated via a User Interface as shown in FIG. 12. Machine vision would then track the location of the "left heel outside" on the pressure image and maintain a higher risk level for this area.

In one embodiment, the machine vision component simply predicts body position (left side, back, right side) based on image processing of the pressure map. Changes in body position result in resetting of the pressure exposure map or risk map.

In one embodiment, the body is divided into a plurality of zones, three zones for example. The location of the body zones is calculated based a simplified machine vision process and the risk model can be adjusted separately for each body zone.

The body zones may be divided along the transverse plane by recognizable features, such as the neck or waist or the like. In addition, left and right zones may be created along the sagittal plane of the body.

In one embodiment, specific areas of concern on the body may be identified (manually or automatically) within a body zone, and correlated with the pressure map. For example, the left and right heels may be identified in a "Feet Zone".

Risk Algorithm

The risk algorithm converts $T_{HR}$ into a quantification of risk. In one embodiment, risk is quantified as a value between 0 and 1, where 0 is the lowest risk and 1 the highest risk. In one embodiment, the model tracks risk in different zones, and may track risk by individual sensel. The risk for a sensel will increase when the pressure is at or above a minimum pressure threshold. The minimum pressure threshold is the interface pressure deemed to be sufficient to allow tissue recovery. In one example, the value is set at 20 mm Hg, but this may be adjusted after further trials and performance testing. If the pressure at the sensel is less than the minimum pressure threshold, the risk will reduce over time. This indicates that the pressure has been sufficiently relieved by repositioning of the patient.

Risk Accumulation

After the acquisition of an initial data set, the sensor data is periodically sampled, for example at one frame per second (a frame is a complete set of interface pressure samples from all the sensors in the array). With each frame, a risk delta is calculated for every sensel as a function of the assigned risk level, the measured pressure, and the time interval between frames (the sampling rate). The current risk value is then updated by the risk delta. The risk value will then constantly fluctuate according to the current risk value, and may continue to accumulate until it reaches a maximum value of 1, or decrease to a minimum value of zero. Therefore, at a constant pressure above a minimum threshold, the risk value will increase linearly with time.

A risk delta may be calculated as a risk coefficient, which is calculated by dividing the maximum risk value (which is for example 1) by the time it takes to achieve high risk for a given pressure. In one embodiment, risk coefficients are expressed as risk/millisecond and become smaller as the $T_{HR}$ increases. In a case where the maximum risk value is 1, a risk coefficient is calculated by the reciprocal of the $T_{HR}$ in milliseconds. Table 3 illustrates how the risk curve described in Table 1 is converted to risk coefficients.

TABLE 3

Risk Coefficients

| Interface Pressure (mmHg) | Time to Accumulate High Risk (mins) | Risk Coefficient (risk/ms) |
|---|---|---|
| 233 | 20 | 8.33E−07 |
| 231 | 30 | 5.56E−07 |
| 218 | 65 | 2.56E−07 |
| 201 | 80 | 2.08E−07 |
| 181 | 95 | 1.75E−07 |
| 164 | 105 | 1.59E−07 |
| 141 | 120 | 1.39E−07 |
| 122 | 135 | 1.23E−07 |
| 100 | 155 | 1.08E−07 |
| 80 | 190 | 8.77E−08 |
| 70 | 230 | 7.25E−08 |

For example, if the current risk value is 0.5 for a given sensel and the interface pressure on the sensel is 201 mmHg, then after one frame (at 1 frame per second) the risk delta will be:

$$1000 * 2.08E{-}07 = 2.08E{-}04$$

If this interface pressure were maintained, it would take approximately 480 seconds at 1 frame per second (8 minutes) for the risk value to increase linearly from 0.5 to 0.6. Higher pressures would result in higher risk deltas, and the risk value would increase faster. Lower pressures would result in lower (or negative) risk deltas and the risk value would increase more slowly or decrease.

In one embodiment, if the THR value has not already been adjusted, the set of risk coefficients may be adjusted for the each risk assessment level (ie. low risk, medium risk, high risk). Therefore, risk deltas are affected by the risk assessment level and body zone risk adjustment as well as by the interface pressure. For example, at a given pressure a patient with a high risk assessment would have a risk coefficient that is double what the coefficient would be for a patient with a low risk assessment. For a body zone risk adjustment, risk coefficients would be calculated for each body area and scaled accordingly if the risk was higher for a particular body area.

When the interface pressure falls below the minimum pressure threshold, the risk value will begin to decrease with negative risk deltas. There is clinical data that suggests 50 mm Hg may be sufficient pressure relief to reduce the risk of tissue breakdown. The minimum pressure threshold may be 40, 30, 25, 20 mm Hg, or less. In one embodiment, as a conservative starting point, 20 mmHg will be used as the minimum pressure threshold.

A study by Makhous et al (2007) proposed that for full tissue perfusion recovery the interface pressure should be relieved and relief maintained for 200 to 300 seconds. Therefore, a clinically accepted recovery period of 300 seconds may be chosen for one embodiment of risk model. This means that the risk model will reduce a sensel's risk value from maximum risk (value of 1) to minimum risk (value of 0) when the interface pressure at a sensel is less than the minimum pressure threshold for the duration of the recovery period. The length of the full recovery period chosen determines the magnitude of the negative risk delta (rate of risk decrease).

In one embodiment, the risk monitor has a reset mechanism which resets the risk level to zero for all sensels. A user may utilize the reset mechanism, for example, if the patient is completely repositioned, such as being rolled over or when resetting the system for a new patient. When a "RESET" or "PATIENT TURNED" action is input and accepted, the risk level will be reset to zero for all sensels. In one embodiment, a change in patient position is detected by machine vision processes and the risk level is reset to zero for all sensels.

Figure 15:
FIG. 15 is a screen shot of one embodiment of a risk map.

In one embodiment, the risk algorithm described herein results in a graphical representation of the accumulated risk value for each sensel in the pressure sensor. The system displays the risk values for all sensels in the form of a risk map, which is updated by the sampling rate or frame rate. The risk map provides an indication of the location and level of risk over the patient's body. In one embodiment, if the risk level in a certain area exceeds a certain level, it may be highlighted, or otherwise modified to catch the attention of a caregiver. As shown for example in FIG. 15, the risk monitor indicates that the patient has high risk at the right shoulder, as indicated by the change in coloration (red for example). Other information may be provided, for example, a pop up timer may be attached to high risk areas indicating how long the area has been at high risk. Grey coloration indicates low risk areas. Areas with no coloration do not have significant interface pressure (below 5 mmHg for example).

In one embodiment, the risk map may be shown as a three-dimensional representation, with higher risk values shown as peaks having a height which is proportional to the magnitude of the risk value.

Patient Turn Management Implementation

In one embodiment, patient turn management is achieved through effective use of the risk map or the pressure exposure map, the interface pressure map, and the turn timer. The turn timer and risk or pressure exposure map are used to track how often the patient is turned or repositioned. The risk map or pressure exposure map and interface pressure map are used to identify body areas with highest risk or pressure exposure and highest interface pressure respectively. The interface pressure map, which shows pressures in real time, may be used to confirm the effectiveness of patient turning or repositioning by indicating that pressure has been relieved and no new high pressure areas have been created.

In one embodiment, patient turn management is achieved through effective use of the turn timer, the interface pressure map, and graphical indicators on the interface pressure map that highlight areas of high pressure exposure. The graphical indicators may provide information on the degree of pressure exposure via call out boxes or pop up windows.

In one embodiment an input device such as a "PATIENT TURN" or "RESET TURN TIMER" button is used to allow the caregiver to indicate that they have turned or repositioned the patient. The input device is used to indicate that the patient has been turned and subsequently the turn timer and pressure exposure or risk values are reset. The input device is appropriately labelled as "Patient Turn", "Reset Turn Clock", "Reset Clock", "Reset Timer", or other text that provides a reasonable indication of the function of this button.

Figure 4:
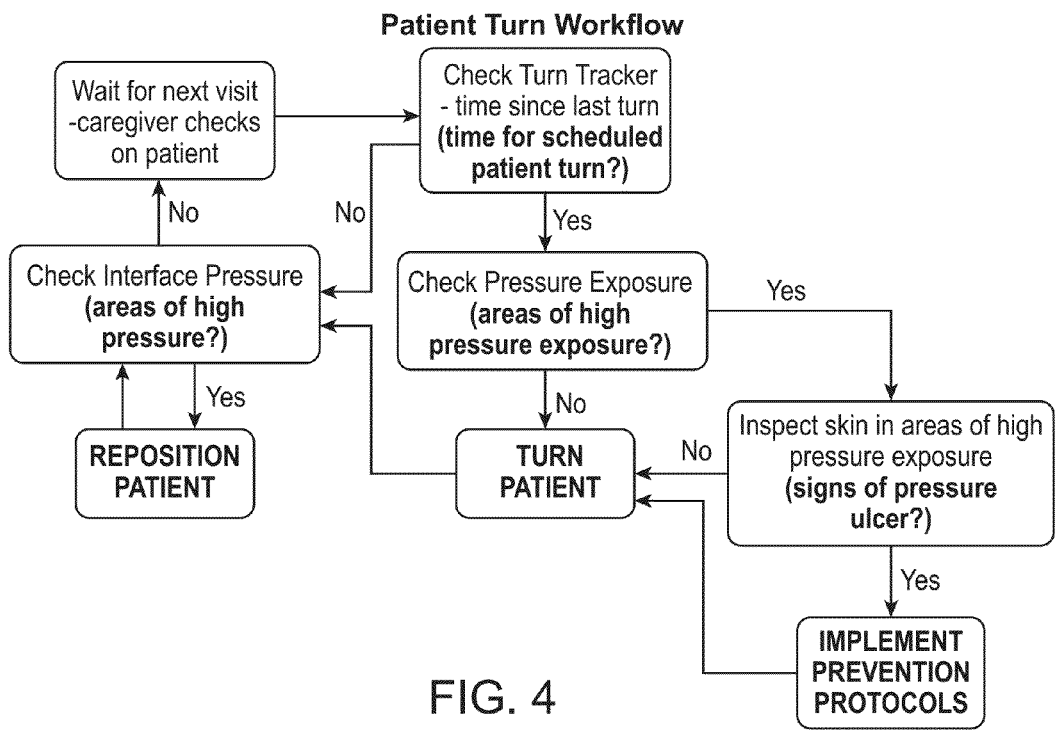
FIG. 4 shows a proposed patient turn workflow that incorporates the present invention.

In one embodiment a new and effective patient turn workflow can be implemented through use of the pressure exposure information, the interface pressure map, and the turn timer. One embodiment of this workflow is illustrated in FIG. 4.

By identifying the patient's body position, a machine vision component allows the turn timer to monitor patient initiated turns in addition to the caregiver initiated turn. Based on this additional turn information the turn timer and pressure exposure map or risk map can be modified to account for patient initiated turns. For example, if the machine vision method identifies that the patient has turned from their back onto their side, the pressure exposure map can be reset in the same way it is reset when the caregiver presses the "RESET TURN TIMER" button.

Figure 5:
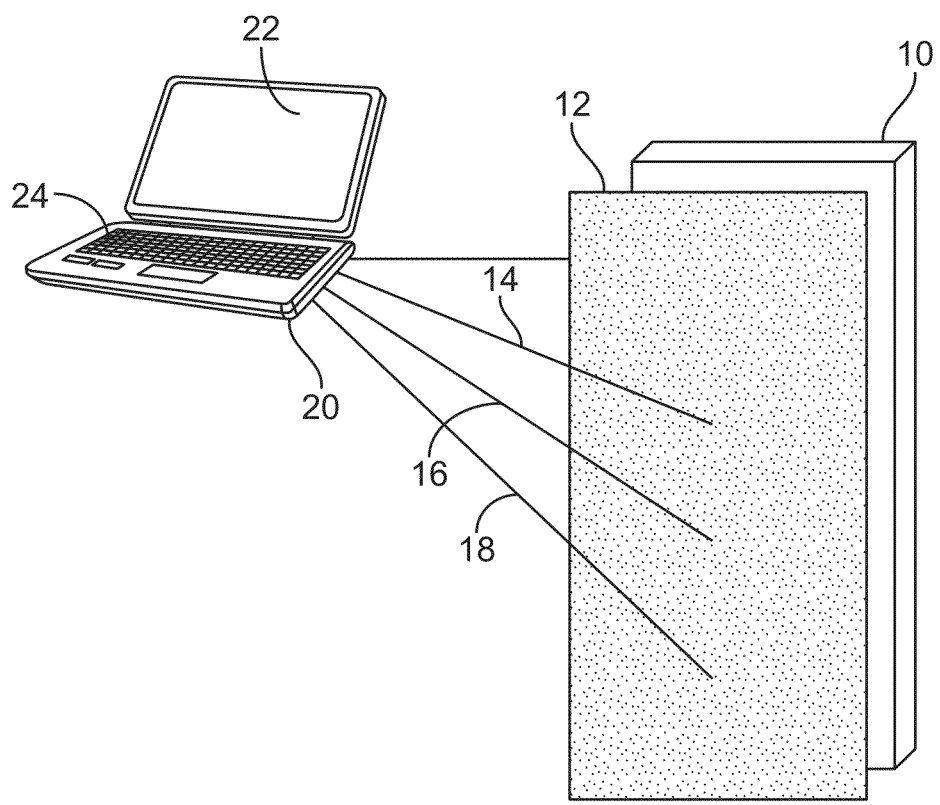
FIG. 5 shows one embodiment of the present invention.

In one embodiment, shown schematically in FIG. 5, a patient turn management system includes a patient support surface (10), which includes an interface pressure mapping system (12), which may comprise a capacitive pressure mapping grid which is well known in the art, and may also include a moisture sensor (14), a shear sensor (16) and a temperature sensor (18). The pressure mapping system comprises a grid which covers all, or substantially all, of the area upon which a patient would be supported on. The pressure mapping system inputs into a general purpose computer (20) which is operating software designed to implement the methods of the present invention, as described above. The software comprises components which implement the various steps of the methods described herein. The computer (20) includes a graphical display (22) and user input devices (24), which are well known in the art. The computer may comprise at least one memory, the memory containing a set of program instructions, and a processor operatively connected to the memory, the processor having components responsive to the program instructions to implement the methods described herein.

In one embodiment, the system of the present invention may utilize moisture, shear, and/or temperature sensor information to modify the scheduled turn interval or reference values used for calculating normalized pressure. For example, the scheduled turn interval may be automatically reduced, for example 15 minutes or 30 minutes, if moisture is detected by the moisture sensor.

Figure 16:
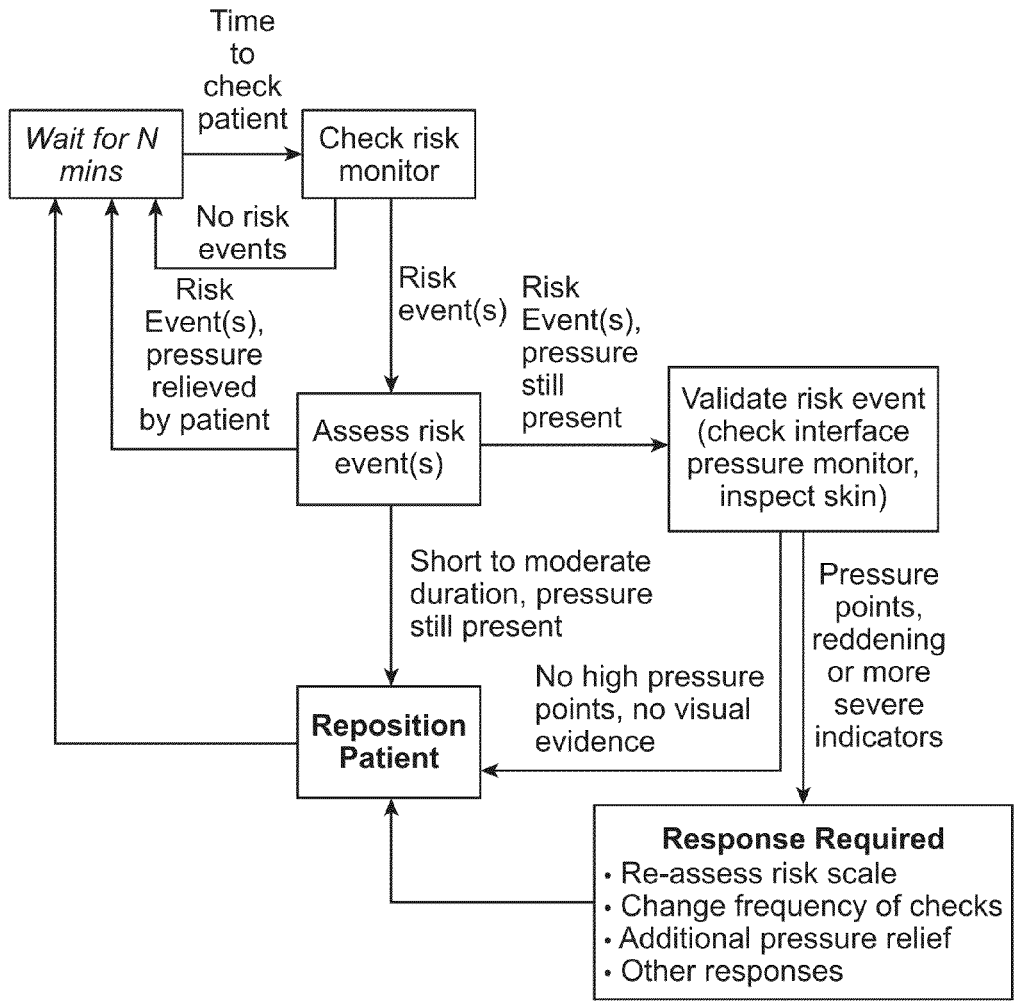
FIG. 16 shows a schematic representation of a method of preventing or reducing pressure ulcer formation.

A real-time interface pressure map may also be provided in conjunction with the risk map to correlate risk areas to the current interface pressure. The combination of real-time pressure map with the risk map can be used to improve the existing clinical pathway for the prevention of pressure ulcers, as shown schematically in FIG. 16. In one aspect, the invention may comprise a method of preventing pressure ulcer formation in a patient, by including a step of adjusting the patient position in response to a risk value or set of risk values exceeding a pre-determined threshold. This may be done manually by a user, or automatically by system actuated devices. The workflow is iterative, where high risk pressure points are validated and relieved by periodically repositioning the patient.

In one embodiment, the system of the present invention may comprise adjustable support surfaces which are operatively connected to the risk or pressure exposure monitor. For example, air bladders may be disposed in a hospital bed mattress and which can be inflated or deflated under control of a system which reacts to a risk value or pressure exposure value produced as described above. Therefore, if the risk map or pressure exposure map shows an elevated level of risk or pressure exposure in a particular zone, the system may inflate or deflate air bladders in or adjacent to that zone in an effort to reduce pressure or to reduce a risk modifier. The system may respond to rate of change of risk or pressure exposure in addition to absolute level of risk or pressure exposure, and react to reduce the rate of accumulation.

The system components shown in the Figures or described above may be or may include a computer or multiple computers. The components may be described in the general context of computer-executable instructions, such as program modules, being executed by a computer. Generally, program modules include routines, programs, objects, components, data structures, etc., that perform particular tasks or implement particular abstract data types.

Those skilled in the art will appreciate that the invention may be practiced with various computer system configurations, including hand-held wireless devices such as mobile phones or PDAs, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer storage media including memory storage devices.

The computer system may include a general purpose computing device in the form of a computer including a processing unit, a system memory, and a system bus that couples various system components including the system memory to the processing unit.

Computers typically include a variety of computer readable media that can form part of the system memory and be read by the processing unit. By way of example, and not limitation, computer readable media may comprise computer storage media and communication media. The system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data.

At a minimum, the memory includes at least one set of instructions that is either permanently or temporarily stored. The processor executes the instructions that are stored in order to process data. The set of instructions may include various instructions that perform a particular task or tasks, such as those shown in the appended flowcharts. Such a set of instructions for performing a particular task may be characterized as a program, software program, software, engine, module, component, mechanism, or tool. The patient monitoring system may include a plurality of software processing modules stored in a memory as described above and executed on a processor in the manner described herein. The program modules may be in the form of any suitable programming language, which is converted to machine language or object code to allow the processor or processors to read the instructions. That is, written lines of programming code or source code, in a particular programming language, may be converted to machine language using a compiler, assembler, or interpreter. The machine language may be binary coded machine instructions specific to a particular computer. Any suitable programming language or combinations of languages may be used in accordance with the various embodiments of the invention.

The processing unit that executes commands and instructions may be a general purpose computer, but may utilize any of a wide variety of other technologies including a special purpose computer, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID processor, smart chip, or any other device or arrangement of devices that is capable of implementing the steps of the processes of the invention.

It should be appreciated that the processors and/or memories of the computer system need not be physically in the same location. Each of the processors and each of the memories used by the computer system may be in geographically distinct locations and be connected so as to communicate with each other in any suitable manner. Additionally, it is appreciated that each of the processor and/or memory may be composed of different physical pieces of equipment.

A user may enter commands and information into the computer through a user interface that includes input devices such as a keyboard and pointing device, commonly referred to as a mouse, trackball or touch pad. Other input devices may include a microphone, joystick, game pad, satellite dish, scanner, voice recognition device, keyboard, touch screen, toggle switch, pushbutton, or the like. These and other input devices are often connected to the processing unit through a user input interface that is coupled to the system bus, but may be connected by other interface and bus structures, such as a parallel port, game port or a universal serial bus (USB).

One or more monitors or display devices may also be connected to the system bus via an interface. In addition to display devices, computers may also include other peripheral output devices, which may be connected through an output peripheral interface. The computers implementing the invention may operate in a networked environment using logical connections to one or more remote computers, the remote computers typically including many or all of the elements described above.

Various networks may be implemented in accordance with embodiments of the invention, including a wired or wireless local area network (LAN) and a wide area network (WAN), wireless personal area network (PAN) and other types of networks. When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Computers may be connected over the Internet, an Intranet, Extranet, Ethernet, or any other system that provides communications. Some suitable communications protocols may include TCP/IP, UDP, or OSI for example. For wireless communications, communications protocols may include Bluetooth, Zigbee, IrDa or other suitable protocol. Furthermore, components of the system may communicate through a combination of wired or wireless paths.

Although many other internal components of the computer are not shown, those of ordinary skill in the art will appreciate that such components and the interconnections are well known. Accordingly, additional details concerning the internal construction of the computer need not be disclosed in connection with the present invention.

As will be apparent to those skilled in the art, various modifications, adaptations and variations of the foregoing specific disclosure can be made without departing from the scope of the invention claimed herein.

What is claimed is:

1. A method of assessing the risk of a patient developing a pressure ulcer, wherein the patient is supported on a support surface, a pressure sensing interface is placed between the patient and the support surface, and the pressure sensing interface has a plurality of sensels, the method comprising the steps of:
   periodically receiving, by a processor, pressure signals indicative of pressure values from the plurality of sensels associated with the pressure sensing interface, the plurality of sensels arranged in a two-dimensional grid;
   processing, by the processor, the pressure signals to obtain the pressure values;
   using a machine vision technique, by the processor, to process the obtained pressure values in order to identify a plurality of body zones of the patient and to assign a set of sensels from the plurality of sensels to each body zone in the identified plurality of body zones of the patient, the machine vision technique tracking the plurality of body zones over time, the tracking comprising adjusting which of the plurality of sensels is included in the set of sensels assigned to each body zone in the identified plurality of body zones of the patient;
   separately for each body zone of the identified plurality of body zones, based on the set of sensels assigned to the body zone:
      deriving, by the processor, a plurality of time-to-high risk (THR) values for the set of sensels from the pressure values, the THR values for the set of sensels being a time to high risk of pressure ulcer formation in the body zone according to the pressure values measured for the set of sensels;
      adjusting, by the processor, the THR values by considering at least one risk modifier;
      converting, by the processor, the risk-adjusted THR values into risk deltas representing changes in risk values over an interval of time, the risk values indicative of a current risk of pressure ulcer formation at the sensel locations correlated with the body zone;
      updating, by the processor, the risk values by the risk deltas; and
      based on the updated risk values, indicating, by the processor, to a user a risk of pressure ulcer formation in the body zone.

2. The method of claim 1, wherein the $T_{HR}$ values are determined by comparing the obtained pressure values to stored pressure vs. time data which comprises a $T_{HR}$ value for a given obtained pressure value.

3. The method of claim 1 wherein the at least one risk modifier comprises at least one data input representative of a risk assessment model.

4. The method of claim 1 wherein the risk deltas are determined by converting the $T_{HR}$ values into risk coefficients.

5. The method of claim 1 wherein the updated risk values for the plurality of sensels are graphically displayed to the user as a risk map image.

6. The method of claim 5 wherein the risk map image is either a two dimensional or a three dimensional image.

7. The method of claim 5 wherein the risk map image is divided into the plurality of body zones which correspond to the patient's anatomical features.

8. The method of claim 7 wherein a risk modifier level is independently determined for each of the body zones.

9. The method of claim 7 wherein a size and location of each body zone is automatically derived from an interface pressure map by automatic identification of the patient's anatomical features from the interface pressure map.

10. The method of claim 1, wherein the $T_{HR}$ values are determined by applying a pre-determined mathematical formula to the pressure values.

11. The method of claim 1 wherein the at least one risk modifier comprises at least one data input representative of shear.

12. The method of claim 1 wherein the at least one risk modifier comprises at least one data input representative of moisture.

13. The method of claim 1 wherein the at least one risk modifier comprises at least one data input representative of temperature.

14. The method of claim 1 wherein the at least one risk modifier comprises at least one data input representative of tissue health.

15. The method of claim 1 wherein the at least one risk modifier comprises at least one data input representative of tissue deflection.

16. The method of claim 1 wherein the at least one risk modifier comprises at least one data input representative of a clinical observation.

17. The method of claim 1 wherein the at least one risk modifier comprises at least one data input representative for at least one combination of a risk assessment model, shear, moisture, temperature, tissue health, tissue deflection, or a clinical observation.

18. The method of claim 1 further comprising reducing the risk values in response to the pressure values being lower than a minimum pressure threshold.

19. The method of claim 1 further comprising resetting the risk values in response to an automatic identification of a patient repositioning.

20. The method of claim 1 further comprising detecting the patient's body position using a machine vision technique and adjusting the risk values in response to the patient's body position.

21. The method of claim 1 further comprising detecting the patient's turns using a machine vision technique and adjusting the risk values in response to the patient's turns.

22. The method of claim 1 further comprising initiating a patient turn or repositioning in response to the risk values exceeding a pre-determined threshold.

23. The method of claim 1 wherein a separate risk value is provided for each sensel.

24. The method of claim 1 wherein the $T_{HR}$ values are displayed to the user.

25. The method of claim 1 wherein each $T_{HR}$ value is an estimate of a duration of time the patient can be exposed to the obtained pressure values before a pressure ulcer begins to form.

26. A method of assessing the risk of a patient developing a pressure ulcer, comprising:
   periodically receiving, by a processor, pressure signals indicative of pressure values from a plurality of sensels associated with a pressure sensing interface, the pressure sensing interface placed between a patient and a support surface supporting the patient and the plurality of sensels arranged in a two-dimensional grid;
   processing, by the processor, the pressure signals to obtain the pressure values;

processing, by the processor, the obtained pressure values to identify a body zone of the patient and to assign a set of sensels from the plurality of sensels to the body zone using a machine vision technique, the machine vision technique tracking the body zone over time and the tracking comprising adjusting which of the plurality of sensels is included in the set of sensels assigned to the body zone;

based on the set of sensels assigned to the body zone:
  deriving, by the processor, a plurality of time-to-high risk (THR) values for the set of sensels from the pressure values, the THR values for the set of sensels being a time to high risk of pressure ulcer formation in the body zone according to the pressure values measured for the set of sensels;
  adjusting, by the processor, the THR values by considering at least one risk modifier;
  converting, by the processor, the risk-adjusted THR values into risk deltas representing changes in risk values over an interval of time, the risk values indicative of a current risk of pressure ulcer formation at the sensel locations correlated with the body zone;
  updating, by the processor, the risk values by the risk deltas; and
  based on the updated risk values, indicating, by the processor, to a user a risk of pressure ulcer formation in the body zone.

\* \* \* \* \*